(12) United States Patent
Dhaliwal

(10) Patent No.: US 6,589,569 B1
(45) Date of Patent: Jul. 8, 2003

(54) METHOD AND COMPOSITION FOR TREATMENT OF PREMENSTRUAL SYNDROME IN WOMEN

(76) Inventor: Kirpal S Dhaliwal, 6181 Eastern Ave., Bell Gardens, CA (US) 90201

( * ) Notice: Subject to any disclaimer, the term of this patent is extended or adjusted under 35 U.S.C. 154(b) by 138 days.

(21) Appl. No.: 09/698,662

(22) Filed: Oct. 30, 2000

(51) Int. Cl.⁷ .............................................. A61K 35/78
(52) U.S. Cl. .................. 424/725; 424/773; 424/774; 424/775; 424/776; 424/777; 424/779
(58) Field of Search ................... 424/725, 773, 424/775, 774, 776, 777, 779

(56) References Cited

U.S. PATENT DOCUMENTS

| | | | | |
|---|---|---|---|---|
| 4,770,880 A | * | 9/1988 | Sasaki et al. ............ | 424/195.1 |
| 5,693,327 A | * | 12/1997 | Shah ....................... | 424/195.1 |

OTHER PUBLICATIONS

Encyclopedia Britannica Online, acessed Aug. 15, 2001, www.search.eb.com/bol/topic?eu+108448&sctn=1.*

* cited by examiner

*Primary Examiner*—Christopher R. Tate
*Assistant Examiner*—Patricia Patten
(74) *Attorney, Agent, or Firm*—Charles H. Thomas

(57) ABSTRACT

A medicinal composition has been created that is useful in the treatment of PMS in human females who experience adverse PMS symptoms. The composition is comprised of an extract of asparagus racemosus. The composition preferably includes about eighty-five parts *Asparagus racemosus* and about five parts each of *Withania sominifera*, *Pedalium murex*, and *Tinospora cordifolia*. The active component of the *Asparagus racemosus* is saponin glucoside (A4). Preferably, the composition is administered in capsular form with each capsule containing about one-half gram of the composition. Two of these capsules are taken three times a day.

1 Claim, 2 Drawing Sheets

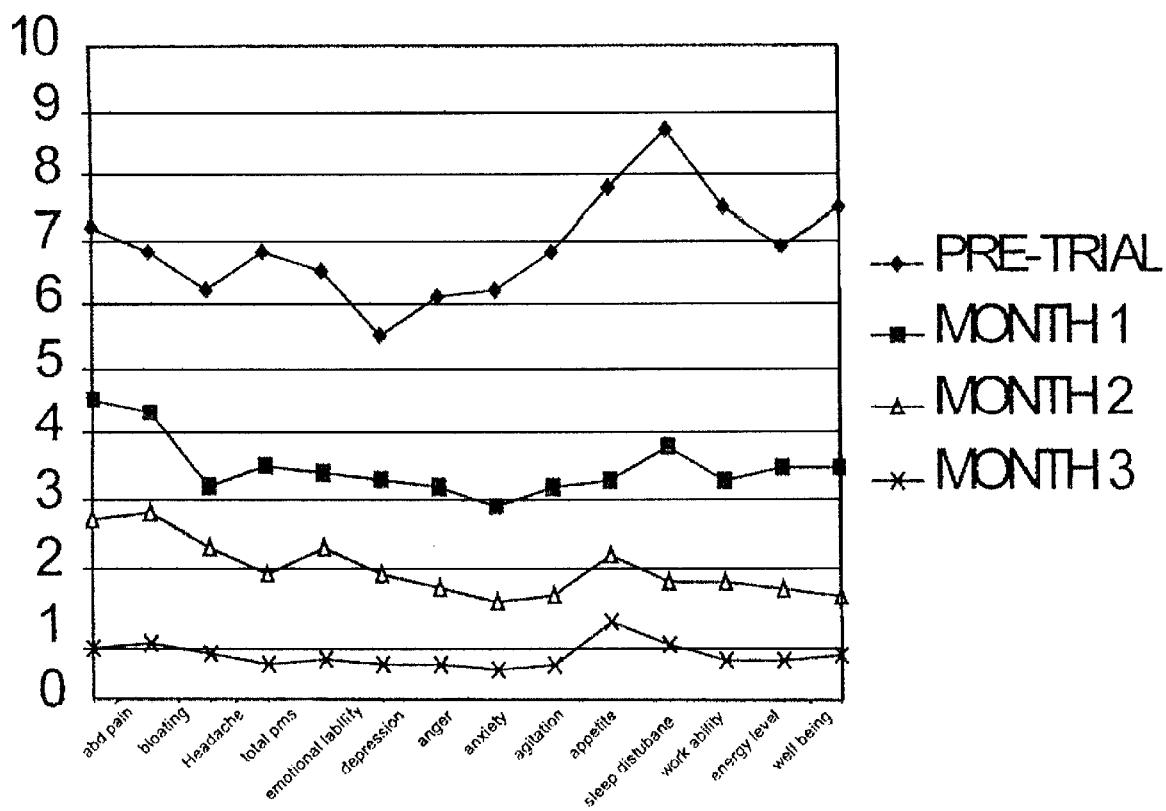
Figure 1 Average Score of PMS Symptoms During Trial

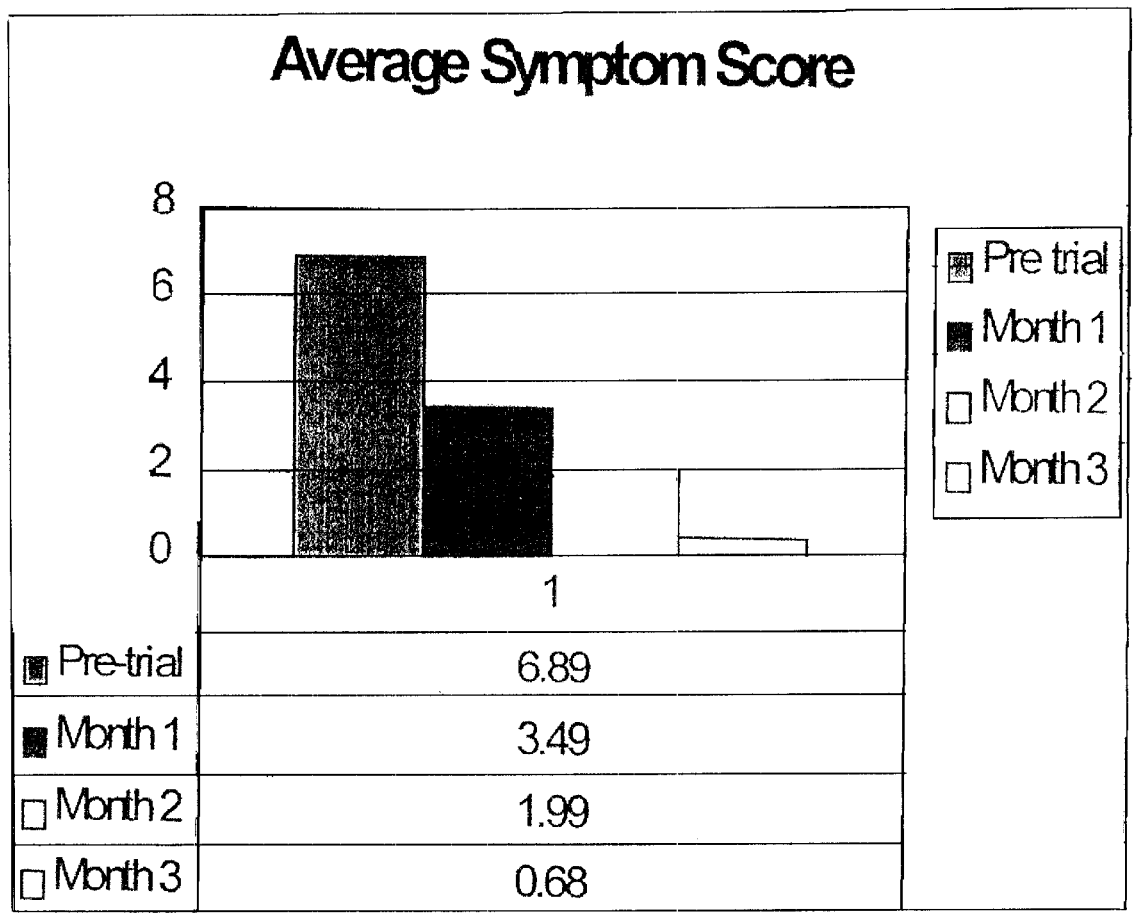
Figure 2 Average of monthly score for all symptoms

METHOD AND COMPOSITION FOR TREATMENT OF PREMENSTRUAL SYNDROME IN WOMEN

BACKGROUND OF THE INVENTION

1. Field of the Invention

The present invention relates to a medicinal composition useful for the treatment of premenstrual syndrome (PMS) and to a method of treatment of PMS.

2. Description of the Prior Art

PMS is a well-known condition that occurs in many women throughout the world. PMS typically involves menstrual cramps, emotional stress and agitation, bloating, and an abnormal amount of menstrual discharge in women for an abnormal duration of time. PMS varies from mild discomfort and emotional problems to complete physical disability. PMS is thought to result from a complex interplay of hormone, imbalance, nutritional deficiencies, and psychological factors. Possible theories of the cause of PMS include a vitamin B6 deficiency, hypoglycemia, hormonal allergy, or a psychosomatic problem.

Almost every woman suffers from PMS at one time or another in her reproductive lifetime. It is estimated that over sixty-seven percent of all women experience significant symptoms of PMS for which they seek some type of intervention. It is further estimated that over thirty-three percent of all women have had medical treatment for PMS sometime in their lives.

The multiple remedies heretofore available to treat PMS simply do not offer relief from that condition. PMS has been the reported cause of discomfort leading to loss of work or school in many women, and has been listed as a significant problem in the offices of a great many gynecologists.

PMS can affect any menstruating woman before and/or during and after her monthly cycle. The presence of PMS creates a variety of physical and psychological complaints. Some of the most common complaints are lower abdominal cramping, bloating, gastrointestinal dysfunction, sleep disturbance, irritability, and depression. No particular pathological process has been found to be the cause of these complaints. It is thought that some women have PMS at various times in their lives as a result of a combination of events or conditions. Until now there has been no single method of treatment that has been developed to effectively combat these symptoms. Thus far, no conventional form of intervention has been proven to show significant success in ameliorating PMS.

SUMMARY OF THE INVENTION

In one broad aspect, the present invention may be considered to be a medicinal composition comprising between about 0.5 grams and about one hundred grams of an extract of *Asparagus racemosus*. The active component of the *Asparagus racemosus* extract is saponin glucoside (A4), which constitutes about five percent of the *Asparagus racemosus* extract by weight. However, saponin glucoside (A4) can also be found in other substances. The foregoing suffix (A4) means that the asparagoside is sarsasapogenin glucoside and that there are four glucoside radicals in the molecules of the saponin glucoside employed. Consequently, in another broad aspect the invention may be considered to be a medicinal composition comprising between about twenty-five milligrams and about five grams of saponin glucoside (A4).

In another broad aspect the invention may be considered to be a method of treating premenstrual syndrome in a human female comprising administering to said human female between about 0.5 grams and about one hundred grams of an extract of *Asparagus racemosus*.

According to the present invention, a medicinal composition has been found that is very effective in treating PMS, even in the most severe cases of that condition. The composition of the invention is an aryuvedic herbal formula based upon a combination of extracts of *Asparagus racemosus* willd (liliaceae) root about eighty-five percent, *Withania sominifera* about five percent, *Pedalium murex* about five percent and *Tinospera cordifolia* about five percent. The foregoing percentages are percentages by weight. *Asparagus racemosus* is in under-shrub which climbs up to between about one and three yards high. It has a stout and creeping rootstock. The powder obtained from the tuberous roots of this plant is a light yellow in color and contains saponins, alkaloids, proteins, starch, tannin, mucilage, and diosgenin. One of the glucosides found in the roots is saponin glucoside (A4). In laboratory animals studies, an alcoholic extract of the root containing saponin glucoside (A4) was shown to produce a specific and competitive block of the pitocin induced contraction and spontaneous uterine motility.

The medicinal composition of the invention is a natural, herbal-based dietary supplement that has effectively reduced, and in some cases, completely eliminated PMS from symptomatic women. A small study of 13 women who had previously suffered severe conditions of PMS was conducted to document the effectiveness of the composition of the invention. Even though the study group was small, the extent of decline of symptoms and the consistency of the effects of administration of the composition of the invention was significant. Although this was not a placebo controlled study, the results are significant in that all study subjects had similar positive responses. A listing of the patients in the sample by number and corresponding age appears in tabular form as Table 1.

TABLE 1

| Patient | Number | BCP Use | Duration PMS | Age | Menarche | G/P |
| --- | --- | --- | --- | --- | --- | --- |
| BM | 1 | no | 10 | 50 | 13 | G1/P1 |
| DS | 2 | yes | 11 | 32 | 15 | G1/P1 |
| NB | 3 | yes | 3 | 40 | 13 | G2/P2 |
| LJ | 4 | yes | 2 | 33 | 14 | G4/P3 |
| DH | 5 | no | 25 | 50 | 14 | G3/P3 |
| PJ | 6 | yes | 10 | 42 | 12 | G3/P2 |
| RH | 7 | no | 8 | 43 | 11 | G2/P2 |
| BH | 8 | yes | 14 | 27 | 12 | G4/P3 |
| CY | 9 | yes | 25 | 40 | 13 | G2/P2 |
| DC | 10 | yes | 20 | 39 | 12 | G4/P4 |
| JW | 11 | yes | 8 | 43 | 13 | G4/P3 |
| LL | 12 | yes | 30 | 43 | 13 | G4/P4 |
| RS | 13 | yes | 26 | 39 | 12 | G3/P2 |

In Table 1 the second column labeled BCP Use indicates whether or not the patient was using birth control pills. The third, labeled Duration PMS, indicates in years the duration of the patient's PMS symptoms. The fifth column labeled Menarche indicates the patients age in years at the time of first menstruation. The last column labeled G/P stands for Gravida/Pera, the first number of which indicates the number of times the patient had been pregnant, and the second number of which indicates the number of live birth deliveries by the patient.

The group studied and indicated in Table 1 consisted of women who had consistently experienced sustained and severe symptoms of PMS that required medical intervention. These conditions were reported by the participants themselves. Severe PMS was defined as PMS that caused symptoms occurring more than 50 percent of menstrual cycles during the past 12 months. The participants were asked to fill out a questionnaire prior to their entrance to the study. This questionnaire requested the participants to numerically rate the various aspects of PMS that they had experienced in the past, with the number ten being highest and the number one being lowest. A zero value would indicate an absence of a symptom altogether. The results of the questionnaires and the average for each aspect of PMS among the participants is set forth in the following Table 2.

All participants took two capsules of the preferred formulation of the composition of the invention on the first day that they noticed symptoms usually associated with their history of PMS. Each capsule contained 0.5 grams of the preferred formulation of the invention, which is comprised of an extract of *Asparagus racemosus*, and preferably other herbs as well. The participants continued to take two capsules, three times daily for four to six days depending on how soon their PMS systems were resolved. They ceased taking the composition of the invention as their symptoms

TABLE 2

| Pat. # | Abdominal pain | Bloating | Headache | Total PMS | Emotional lability | Depression | Anger | Anxiety | Agitation | Appetite | Sleep Disturbance | Work ability | Energy level | Well being |
|---|---|---|---|---|---|---|---|---|---|---|---|---|---|---|
| 1 | 7 | 6 | 3 | 8 | 7 | 4 | 2 | 4 | 7 | 7 | 6 | 7 | 7 | 8 |
| 2 | 8 | 4 | 3 | 6 | 8 | 1 | 8 | 5 | 8 | 7 | 7 | 8 | 6 | 8 |
| 3 | 6 | 5 | 3 | 7 | 8 | 7 | 6 | 7 | 5 | 8 | 9 | 8 | 8 | 8 |
| 4 | 7 | 6 | 7 | 5 | 4 | 5 | 5 | 6 | 7 | 9 | 10 | 6 | 3 | 7 |
| 5 | 5 | 7 | 6 | 7 | 6 | 5 | 6 | 5 | 6 | 8 | 8 | 7 | 6 | 7 |
| 6 | 8 | 6 | 6 | 7 | 4 | 4 | 3 | 5 | 5 | 7 | 8 | 7 | 6 | 7 |
| 7 | 9 | 9 | 9 | 8 | 8 | 7 | 8 | 8 | 9 | 7 | 9 | 9 | 7 | 8 |
| 8 | 7 | 6 | 6 | 6 | 7 | 7 | 6 | 7 | 7 | 8 | 9 | 7 | 7 | 6 |
| 9 | 7 | 7 | 6 | 6 | 6 | 5 | 5 | 5 | 6 | 7 | 9 | 7 | 7 | 7 |
| 10 | 6 | 7 | 7 | 6 | 6 | 4 | 7 | 8 | 6 | 8 | 9 | 6 | 8 | 7 |
| 11 | 8 | 8 | 7 | 7 | 6 | 7 | 7 | 6 | 6 | 8 | 9 | 8 | 8 | 8 |
| 12 | 8 | 9 | 9 | 8 | 8 | 8 | 9 | 9 | 9 | 8 | 10 | 9 | 9 | 8 |
| 13 | 8 | 9 | 9 | 8 | 7 | 7 | 7 | 6 | 7 | 9 | 10 | 8 | 8 | 9 |
| Sum | 94 | 89 | 81 | 89 | 85 | 71 | 79 | 81 | 88 | 101 | 113 | 97 | 90 | 98 |
| Average | 7.23 | 6.85 | 6.23 | 6.85 | 6.54 | 5.46 | 6.08 | 6.23 | 6.77 | 7.77 | 8.69 | 7.46 | 6.92 | 7.54 |

The potential side effects of the study were discussed with the participants and, following their consent, they were entered into a voluntary three-month trial. Participants were advised that they could not continue to take either prescription drugs or over-the-counter preparations for PMS during the study. All participants, were cautioned to avoid pregnancy during the trial and that they would be terminated from the study should they become pregnant during the trial.

abated, or after six days, whichever came first. At the end of each cycle they were given the same questionnaire as before and again asked to rate the aspects of PMS that they had just experienced during the previous cycle while taking the medication of the invention. The results and averages from these questionnaires for the first, second and third cycles of the study are set forth as follows in Tables 3, 4, and 5, respectively.

TABLE 3

| Pat. # | Abdominal pain | Bloating | Headache | Total PMS | Emotional lability | Depression | Anger | Anxiety | Agitation | Appetite | Sleep Disturbance | Work ability | Energy level | Well being |
|---|---|---|---|---|---|---|---|---|---|---|---|---|---|---|
| 1 | 1 | 2 | 1 | 1 | 1 | 1 | 1 | 1 | 1 | 1 | 1 | 1 | 1 | 1 |
| 2 | 1 | 4 | 1 | 2 | 1 | 1 | 1 | 1 | 1 | 2 | 3 | 1 | 1 | 1 |
| 3 | 3 | 3 | 2 | 2 | 1 | 3 | 3 | 2 | 3 | 3 | 2 | 3 | 3 | 3 |
| 4 | 2 | 1 | 0 | 3 | 4 | 3 | 2 | 2 | 2 | 3 | 4 | 4 | 3 | 3 |
| 5 | 3 | 2 | 3 | 4 | 3 | 2 | 1 | 2 | 2 | 3 | 2 | 2 | 3 | 2 |
| 6 | 3 | 3 | 2 | 2 | 2 | 4 | 3 | 2 | 3 | 3 | 3 | 3 | 3 | 3 |
| 7 | 7 | 7 | 6 | 6 | 6 | 5 | 4 | 5 | 6 | 6 | 7 | 8 | 7 | 7 |
| 8 | 5 | 5 | 3 | 3 | 3 | 2 | 2 | 3 | 3 | 3 | 6 | 5 | 5 | 6 |
| 9 | 5 | 4 | 4 | 3 | 3 | 3 | 3 | 3 | 3 | 3 | 4 | 3 | 4 | 3 |
| 10 | 8 | 7 | 5 | 4 | 3 | 3 | 3 | 2 | 2 | 2 | 2 | 1 | 4 | 4 |
| 11 | 8 | 8 | 7 | 7 | 8 | 9 | 9 | 9 | 8 | 7 | 7 | 7 | 7 | 8 |
| 12 | 5 | 4 | 2 | 2 | 4 | 2 | 4 | 3 | 3 | 3 | 4 | 2 | 2 | 2 |
| 13 | 7 | 6 | 6 | 6 | 5 | 5 | 5 | 3 | 4 | 4 | 4 | 3 | 3 | 3 |
| sum | 58 | 56 | 42 | 45 | 44 | 43 | 41 | 38 | 41 | 43 | 49 | 43 | 46 | 46 |
| Average | 4.46 | 4.31 | 3.23 | 3.46 | 3.38 | 3.31 | 3.15 | 2.92 | 3.15 | 3.31 | 3.77 | 3.31 | 3.54 | 3.54 |

TABLE 4

| Pat. # | Abdominal pain | Bloating | Headache | Total PMS | Emotional lability | Depression | Anger | Anxiety | Agitation | Appetite | Sleep Disturbance | Work ability | Energy level | Well being |
|---|---|---|---|---|---|---|---|---|---|---|---|---|---|---|
| 1 | 1 | 2 | 0 | 1 | 1 | 1 | 1 | 1 | 1 | 1 | 1 | 1 | 1 | 1 |
| 2 | 1 | 1 | 1 | 1 | 2 | 1 | 2 | 1 | 1 | 2 | 1 | 1 | 1 | 2 |
| 3 | 1 | 5 | 3 | 1 | 1 | 1 | 1 | 1 | 2 | 2 | 1 | 1 | 2 | 1 |
| 4 | 2 | 2 | 2 | 2 | 2 | 2 | 2 | 2 | 2 | 3 | 3 | 1 | 3 | 2 |
| 5 | 2 | 2 | 2 | 1 | 2 | 1 | 0 | 0 | 0 | 2 | 1 | 0 | 0 | 0 |
| 6 | 2 | 2 | 1 | 1 | 2 | 2 | 2 | 2 | 2 | 3 | 2 | 1 | 1 | 4 |
| 7 | 5 | 4 | 5 | 4 | 4 | 3 | 3 | 3 | 3 | 3 | 5 | 6 | 3 | 3 |
| 8 | 5 | 5 | 4 | 3 | 3 | 3 | 2 | 2 | 2 | 3 | 2 | 3 | 3 | 2 |
| 9 | 2 | 2 | 2 | 2 | 1 | 1 | 1 | 1 | 0 | 0 | 0 | 0 | 0 | 0 |
| 10 | 3 | 2 | 2 | 2 | 3 | 2 | 1 | 1 | 2 | 2 | 2 | 2 | 1 | 2 |
| 11 | 4 | 3 | 3 | 2 | 4 | 3 | 3 | 2 | 2 | 5 | 3 | 4 | 4 | 4 |
| 12 | 3 | 3 | 3 | 3 | 3 | 3 | 3 | 3 | 3 | 1 | 1 | 2 | 2 | 2 |
| 13 | 4 | 3 | 2 | 2 | 2 | 2 | 1 | 1 | 1 | 2 | 2 | 2 | 1 | 1 |
| Average | 2.69 | 2.77 | 2.31 | 1.92 | 2.31 | 1.92 | 1.6 | 1.54 | 1.62 | 2.23 | 1.85 | 1.85 | 1.69 | 1.62 |

TABLE 5

| Pat. # | Abdominal pain | Bloating | Headache | Total PMS | Emotional lability | Depression | Anger | Anxiety | Agitation | Appetite | Sleep Disturbance | Work ability | Energy level | Well being |
|---|---|---|---|---|---|---|---|---|---|---|---|---|---|---|
| 1 | 1 | 2 | 1 | 1 | 1 | 1 | 1 | 1 | 1 | 1 | 1 | 1 | 1 | 1 |
| 2 | 0 | 0 | 1 | 0 | 0 | 0 | 0 | 0 | 0 | 2 | 0 | 1 | 1 | 0 |
| 3 | 0 | 0 | 0 | 0 | 0 | 0 | 0 | 0 | 0 | 2 | 0 | 0 | 1 | 1 |
| 4 | 1 | 1 | 1 | 1 | 1 | 1 | 1 | 1 | 1 | 1 | 1 | 1 | 1 | 1 |
| 5 | 1 | 1 | 1 | 1 | 1 | 1 | 1 | 1 | 1 | 1 | 1 | 1 | 1 | 1 |
| 6 | 1 | 1 | 1 | 1 | 1 | 1 | 1 | 1 | 1 | 1 | 1 | 0 | 0 | 0 |
| 7 | 2 | 2 | 1 | 1 | 1 | 1 | 1 | 1 | 1 | 2 | 1 | 1 | 2 | 2 |
| 8 | 0 | 1 | 0 | 0 | 0 | 0 | 0 | 0 | 0 | 2 | 2 | 0 | 0 | 0 |
| 9 | 1 | 1 | 1 | 1 | 1 | 1 | 1 | 1 | 1 | 2 | 1 | 1 | 1 | 1 |
| 10 | 1 | 0 | 0 | 0 | 0 | 0 | 1 | 0 | 0 | 0 | 0 | 1 | 0 | 0 |
| 11 | 1 | 1 | 1 | 1 | 1 | 1 | 0 | 0 | 0 | 0 | 0 | 0 | 0 | 0 |
| 12 | 0 | 0 | 0 | 0 | 1 | 0 | 0 | 0 | 1 | 0 | 1 | 1 | 0 | 1 |
| 13 | 1 | 1 | 1 | 0 | 0 | 0 | 0 | 0 | 0 | 2 | 2 | 0 | 0 | 1 |
| Average | 0.77 | 0.85 | 0.69 | 0.54 | 0.62 | 0.54 | 0.54 | 0.46 | 0.54 | 1.23 | 0.85 | 0.62 | 0.62 | 0.69 |

All of the participants who entered the study completed three menstrual cycles while taking the composition of the invention. There were no noticed or reported side effects, adverse reactions, or allergic reactions. All participants reported consistent, positive responses during the trial period, as is evident from Tables 2, 3, 4, and 5. The average score of PMS symptoms was plotted against time. The results revealed significant decreases in the reported complaints over the three-month period of study, as indicated in the accompanying drawing figures.

DESCRIPTION OF THE DRAWINGS

FIG. 1 is a graph showing the average score of PMS symptoms during the trial period.

FIG. 2 is a bar graph of the average symptoms over the three-month trial period.

As is evident from the foregoing tables and drawing figures, the overall average of the several PMS symptoms was almost seven at the time of the pretrial interview. By the end of the study that average had dropped to less than 1.

EXAMPLES OF PRODUCING THE COMPOSITION OF THE INVENTION

EXAMPLE 1

The extract which forms the medicinal composition of the invention may be produced by boiling *Asparagus racemosus* root powder in water at a ratio of one part powder to four parts water until the water volume is reduced to one quarter of its original volume. This solution is filtered using a 100 micron screen. The solids are discarded and the water extract is saved. The following dry powder components are then blended in the proportions indicated: *Asparagus racemosus* eighty-five percent, *Withania sominifera* five percent, *Pedalium murex* five percent, *Tinospora cordifolia* five percent. This blended mixture of dry herbs is then mixed with the water extract previously produced in a ratio of 14 parts dry powder mixture to 1 art extract and allowed to soak 48 hours, at a minimum. This soaked powder is then dried at one hundred thirty degrees Fahrenheit to a moisture content of seven percent or less.

The foregoing steps of boiling, filtering, blending and mixing are repeated five times in succession. At the end of the fifth time the powder is packaged, preferably in capsules containing about 0.5 grams each of the dried extract composition.

EXAMPLE 2

A powdered blend of eighty-five percent *Asparagus racemosus*, five percent *Withania sominifera*, five percent *Pedalium murex*, and five percent *Tinospora cordifolia* are mixed in water at a ratio of one part powder to four parts water. This mixture is boiled until the volume is reduced to one-quarter of its original volume. The solution is filtered using a 100 micron screen. The solids are discarded and the water extract is saved. A corn starch powder is then mixed with the water extract in a ratio of 14 parts powder to 1 part extract and allowed to soak for a minimum of eight hours. This soaked powder is dried at one hundred thirty degrees Fahrenheit to a moisture content of seven percent or less. The steps of boiling, filtering, mixing and drying are repeated five times. At the end of the fifth repetition the powdered material is ground and packaged, preferably in capsules each containing about 0.5 grams of the composition.

Undoubtedly, numerous variations and modifications of the invention will become readily apparent to those familiar with extraction processes and the administration of medication. Accordingly, the scope of the invention should not be construed as limited to the specific formulations and steps of administration described, but rather is defined in the claims appended hereto.

I claim:

1. A medicinal composition comprising an extract of *Asparagus racemosus* root powder produced by boiling root powder of *Asparagus racemosus* in water, filtering said solution to separate solids therefrom, discarding said solids; and adding further herbs, including *Asparagus racemosus* to said solution to produce said extract, and thereafter evaporating said water to produce between about 0.5 grams and about 100 grams of said powdered extract.

* * * * *